US006971987B1

(12) United States Patent
Chung

(10) Patent No.: US 6,971,987 B1
(45) Date of Patent: Dec. 6, 2005

(54) APPARATUSES FOR SECURING MEDICAL DEVICES TO HUMANS AND METHODS FOR FACILITATING THE MANIPULATION OF SECURED MEDICAL DEVICES

(75) Inventor: Sydney S. C. Chung, Tai Po (HK)

(73) Assignee: The Chinese University of Hong Kong, Hong Kong (HK)

( * ) Notice: Subject to any disclaimer, the term of this patent is extended or adjusted under 35 U.S.C. 154(b) by 0 days.

(21) Appl. No.: 10/251,906

(22) Filed: Sep. 20, 2002

Related U.S. Application Data

(60) Provisional application No. 60/324,074, filed on Sep. 21, 2001.

(51) Int. Cl.[7] ............................................... A61B 1/00
(52) U.S. Cl. ..................................................... 600/102
(58) Field of Search ............................... 600/102, 131, 600/114, 101

(56) References Cited

U.S. PATENT DOCUMENTS

| 3,282,482 | A | * | 11/1966 | Scharsu ...................... 224/605 |
| 3,765,401 | A | * | 10/1973 | Vass ........................... 604/180 |
| 3,895,629 | A | * | 7/1975 | Snyder ......................... 604/19 |
| 4,248,229 | A | * | 2/1981 | Miller .......................... 604/174 |
| 4,265,561 | A | * | 5/1981 | Heckele ......................... 403/3 |
| 4,316,461 | A | * | 2/1982 | Marais et al. ............... 604/179 |
| 4,416,664 | A | * | 11/1983 | Womack ..................... 604/174 |
| 4,801,059 | A | * | 1/1989 | Hayes ......................... 224/240 |
| 4,899,730 | A | * | 2/1990 | Stennert et al. ............. 600/102 |
| 5,088,634 | A | * | 2/1992 | MacLaren ................... 224/665 |
| 5,728,047 | A | * | 3/1998 | Edoga ......................... 600/227 |
| 5,728,070 | A | * | 3/1998 | Walker et al. .............. 604/179 |
| 5,879,289 | A | * | 3/1999 | Yarush et al. ............... 600/179 |
| 6,106,456 | A | * | 8/2000 | Storz .......................... 600/102 |
| 6,217,511 | B1 | | 4/2001 | Held ........................... 600/131 |
| 6,237,821 | B1 | * | 5/2001 | Owen .......................... 224/200 |

* cited by examiner

Primary Examiner—John P. Leubecker
(74) Attorney, Agent, or Firm—Fulbright & Jaworski L.L.P.

(57) ABSTRACT

Methods and apparatuses that can be used to secure a medical device, such as an endoscope, to a human. As a result, the human is able to manipulate the medical device through the movement of his body without always having to use his hands. In securing an endoscope, for example, in this fashion, the surgeon's hands are free to manipulate and control accessory devices that can be used with the endoscope. The present apparatuses include a human-attachment element, which may take the form of a harness, and an endoscope-attachment element.

5 Claims, 7 Drawing Sheets

APPARATUSES FOR SECURING MEDICAL DEVICES TO HUMANS AND METHODS FOR FACILITATING THE MANIPULATION OF SECURED MEDICAL DEVICES

This application claims priority to U.S. Provisional Patent Application Ser. No. 60/324,074 filed Sep. 21, 2001, the entire text of which is specifically incorporated by reference without disclaimer.

BACKGROUND OF THE INVENTION

1. Field of the Invention

The present invention relates generally to medical devices and manipulation of the same. More particularly, it concerns methods and apparatuses useful in manipulating medical devices such as endoscopes and any accessories thereof. It concerns, for example, an apparatus that can be used to secure a medical device, such as an endoscope, to a surgeon such that the surgeon may manipulate the medical device at least in part through his body movements, and such that the surgeon may manipulate accessories to the medical device using his hands.

2. Description of Related Art

Currently endoscopes are held in the hand. A surgeon can control the deflection of the tip of the endoscope using a wheel or wheels that are provided on the control handle of the endoscope, near its proximal end. A surgeon can also control rotation of the tip through torque that is applied by twisting the control handle using wrist movement. Insertion and removal of the endoscope is usually achieved by the other hand, which holds the insertion tube of the endoscope. Both hands of the endoscopist are thus occupied with control of the endoscope.

Accessories (such as cutting tools and sensors, which are useful for therapeutic and diagnostic purposes, respectively) are usually inserted into the patient through the instrument channel of the endoscope. While the insertion of such accessories is under the guidance of the surgeon, the insertion and/or withdrawal of a given accessory cannot be precisely controlled by the surgeon if he is simultaneously controlling the position of the insertion tube within the patient as described above. As a result, the control of the accessories themselves are usually performed by endoscopy nurses or assistants. The precise maneuvers necessary for complex procedures are thus difficult or impossible as the endoscope and the accessories, controlled by two different persons, have to move in a coordinated manner.

For complex therapeutic procedures, more than one accessory may be necessary. The coordinated movement of these accessories is necessary for the precise execution of operations involving endoscopes. Again, this is difficult to achieve if the endoscopist's hands are preoccupied with holding and controlling the endoscope and cannot be spared to control the accessories.

SUMMARY OF THE INVENTION

The present methods and apparatuses overcome the shortcomings of traditional methods of manipulating medical devices such as endoscopes. The present apparatuses can be used to secure an endoscope to a surgeon in a way that allows the surgeon to manipulate the endoscope through the movement of his body, and not necessarily his hands, which are then free to manipulate the accessories that are used with the endoscope. As a result, the present methods and apparatuses provide an easier way to coordinate precise manipulation of medical devices such as endoscopes and accessories thereto, resulting in safer and more timely interventions.

BRIEF DESCRIPTION OF THE DRAWINGS

The following drawings form part of the present specification and are included to further demonstrate certain aspects of the present methods and apparatuses. The present methods and apparatuses may be better understood by reference to one or more of these drawings in combination with the description of illustrative embodiments presented herein. These drawings illustrate by way of example and not limitation, and they use like references to indicate similar elements.

DESCRIPTION OF ILLUSTRATIVE EMBODIMENTS

Figure 1:
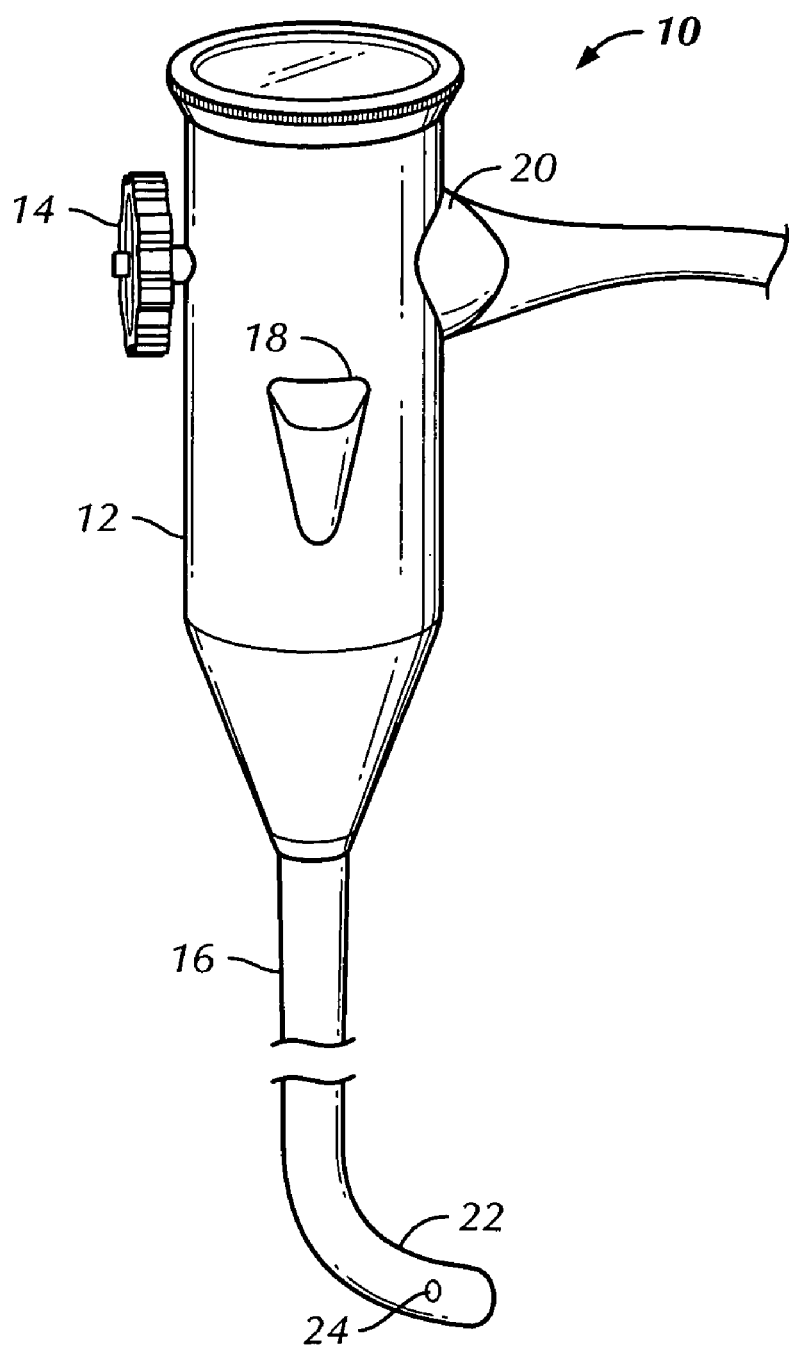
FIG. 1 is a front view of an endoscope that may be secured to a human using one of the present endoscope-securing apparatuses.

As a preliminary matter, it should be noted that in this document (including the claims), the terms "comprise" (and any form thereof, such as "comprises" and "comprising"), "have" (and any form thereof, such as "has" and "having"), and "include" (and any form thereof, such as "includes" and "including") are open-ended transitional terms. Thus, a thing (such as an apparatus or a method) that "comprises," "has," or "includes" one or more elements possesses those one or more elements, but is not limited to only possessing those one or more elements. For example, an apparatus "comprising" a human-attachment element and an endoscope-attachment element is an apparatus that has, but is not limited to only having, the described elements. In other words, the apparatus possesses the two elements, but is not excluded from possessing additional elements or features that are not listed.

A surgeon may use one of the present apparatuses to secure a medical device to his body in a way that allows him to manipulate the medical device without always having to use his hands. That is, using one of the present apparatuses, it is possible to secure a medical device to a surgeon such that the surgeon can manipulate the device through one or more movements of his body that do not involve his hands (i.e., hands-free movements). Such hands-free movements can involve, for example, the surgeon walking toward or away from the patient; the surgeon moving his body toward or away from the patient without moving his feet; the surgeon twisting his body; etc.—all of which translate into and cause movement of the medical device.

Although the medical device described in the greatest detail in this document is the endoscope, it will be understood by those of skill in the art that this disclosure is not limited to apparatuses that can be used to secure only endoscopes to humans. Rather, this disclosure contemplates securing any of a variety of different devices to a human using the present apparatuses. Such devices include catheters, sheaths, cutting tools, sensors, delivery devices for intravascular devices such as stents, filters, coils, or other occluders, and the like.

With the present apparatuses and methods, a surgeon is able to manipulate medical devices like endoscopes in a way that allows his hands to be free for other purposes. That is, a surgeon using one of the present apparatuses can secure a medical device such as an endoscope to his body, use at least some hands-free movements to manipulate the endoscope, and use his hands to control accessories that are utilized cooperatively with the endoscope. This manipulation of one or more accessories is possible because the present methods and apparatuses free up the surgeon's hands to a greater extent than formerly possible using traditional methods. These accessories include medical devices such as, for example, cutting tools, baskets, polyp removers, contrast-injection devices, balloons, catheters, sheaths, flushing devices, sensors, and the like.

Turning to FIG. 1, an endoscope 10 is shown. Endoscope 10 includes body 12, control mechanism 14 (represented as a single knob) projecting from body 12, insertion tube 16 extending away from body 12, accessory-acceptance projection 18 (one example of which is known in the art as an "accessory port") projecting from body 12, and optical transmission projection 20 (one example of which is known in the art as an "umbilical cord") projecting from body 12. Insertion tube 16 includes tip 22. Control mechanism 14 may be utilized to control the deflection of tip 22. Insertion tube 16 may be provided with one or more (e.g., two) lumens, or passageways (e.g., channels). These passageways may be accessible through accessory-acceptance projection 18. A surgeon may insert an accessory into accessory-acceptance projection 18 and into one of the passageways within insertion tube 16. This is possible when accessory-acceptance projection 18 is in communication with a particular passageway. Such communication is accomplished by providing a path from accessory-acceptance projection 18 to the particular passageway within insertion tube 16. Multiple such paths may be provided in a given accessory-acceptance projection, and multiple accessory-acceptance projection may be provided on a given endoscope. Insertion tube opening 24 is provided near tip 22. Accessories may extend out of opening 24 during a procedure using endoscope 10. One or more openings 24 may be provided within insertion tube 16.

Furthermore, the length of an accessory placed into accessory-acceptance projection 18 may need to be adjusted from its conventional length (e.g., making it shorter or longer) so as to make it easier for the surgeon to reach the accessory.

Although not shown, those of skill in the art will understand that at or near tip 22, a lens and a light source may be provided that permits viewing of internal body structures. This viewing may be accomplished using a camera (not shown) provided within body 12 of endoscope 10, an image processing apparatus (not shown), and a viewing apparatus (not shown). One or more cables (such as fiber optic cables) may be provided that connect the lens and light source to the camera. Furthermore, the one or more cables may extend through optical transmission projection 20 to the image processing apparatus.

Figure 3:
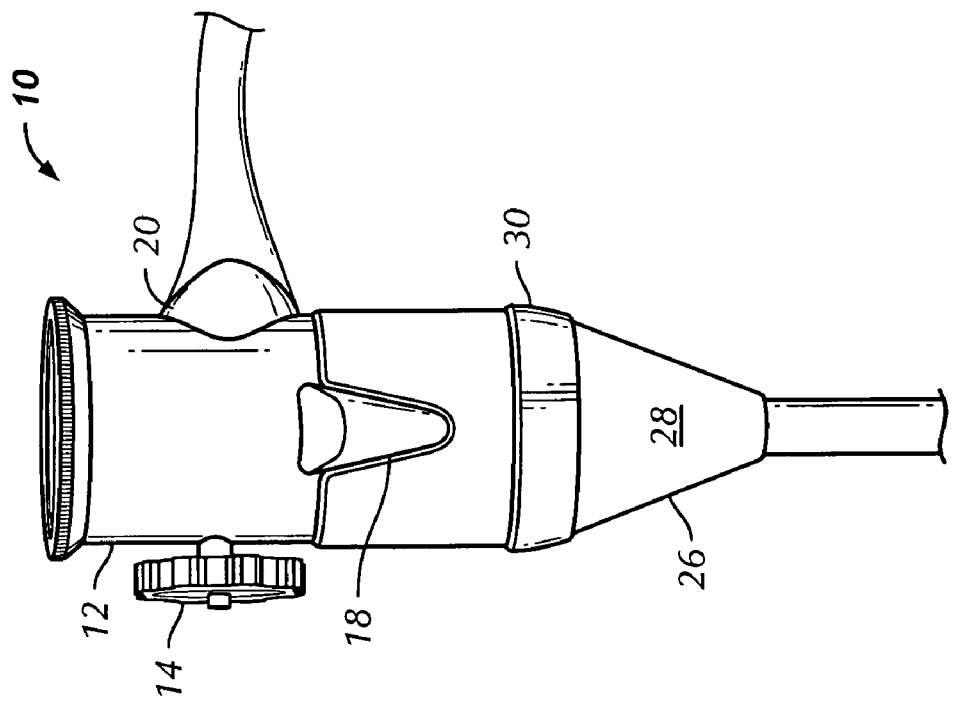
FIG. 3 is a front view of one embodiment of an endoscope-securing element of one of the present endoscope-securing apparatuses, which endoscope-securing element is depicted as being in contact with an endoscope.
Figure 2:
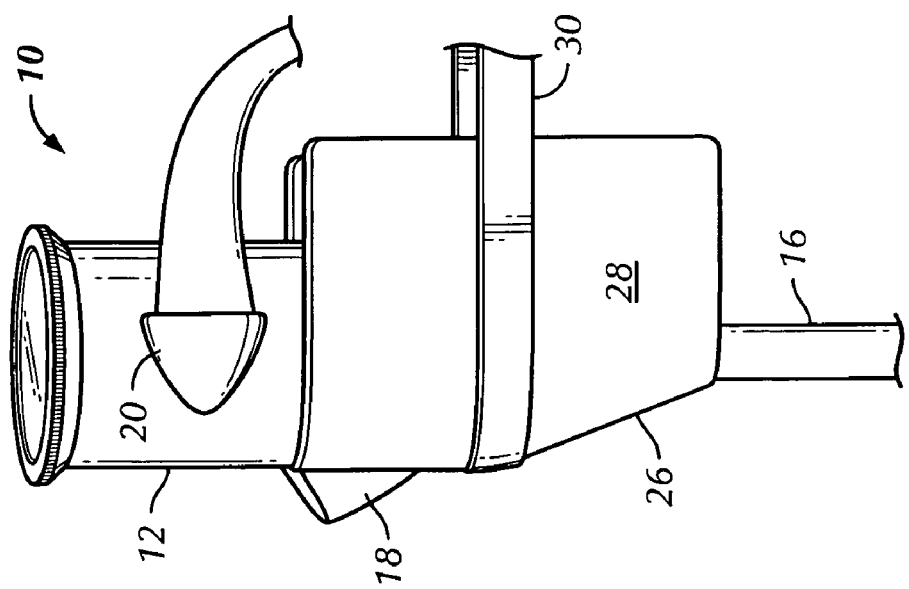
FIG. 2 is a side view of the endoscope depicted in FIG. 1.

Using one of the present apparatuses, endoscope 10 may be secured to a human. FIG. 2 illustrates a side view of endoscope-attachment element 26 in contact with endoscope 10. A front view of the same arrangement is shown in FIG. 3. Endoscope-attachment element 26 is adapted to be coupled to human-attachment element 40, depicted in FIG. 4. That is, endoscope-attachment element 26 may include a piece of material 28 to which a strap 30 may be attached. Strap 30—and, thus, endoscope-attachment element 26—may be coupled to human-attachment element 40 using any suitable means, including buckles, VELCRO, adhesive, knot(s), tape, interlocking parts (e.g., snaps), or the like. Together, endoscope-attachment element 26 and human-attachment element 28 form an endoscope-securing apparatus 60 that can be used to secure endoscope 10 to a human as shown in FIG. 5.

Although not shown, endoscope-attachment element 26 may take any form suited to achieving the attachment of an endoscope to a human in conjunction with human-attachment element 40. For example, endoscope-attachment element 26 may be a basket-like element formed from cloth or cloth-like material into which endoscope 10 may be placed and rest securely via, e.g., gravitational forces. Additional measures may be implemented to secure endoscope 10 within endoscope-attachment element 26, such as forming a suitable basket or housing out of a material that enhances the friction between the endoscope and the basket or housing, thereby increasing the likelihood that movement of the basket or housing will translate in some fashion to movement of the endoscope without slippage occurring. Another such measure would be to secure the endoscope within the endoscope-attachment element 26 using any of the means identified above for use in coupling strap 30 to human-attachment element 40. Further, such a basket-like element (a housing, for example) may be coupled to human-attachment element 40 using any suitable means, including those described above. Human-attachment element 40 and endoscope-attachment element 26 may also be formed from the same piece of material. Such a configuration of one of the present endoscope-securing apparatuses is intended to fall within the meaning of an endoscope-attachment element that is adapted to be coupled to a human-attachment element.

Figure 4:
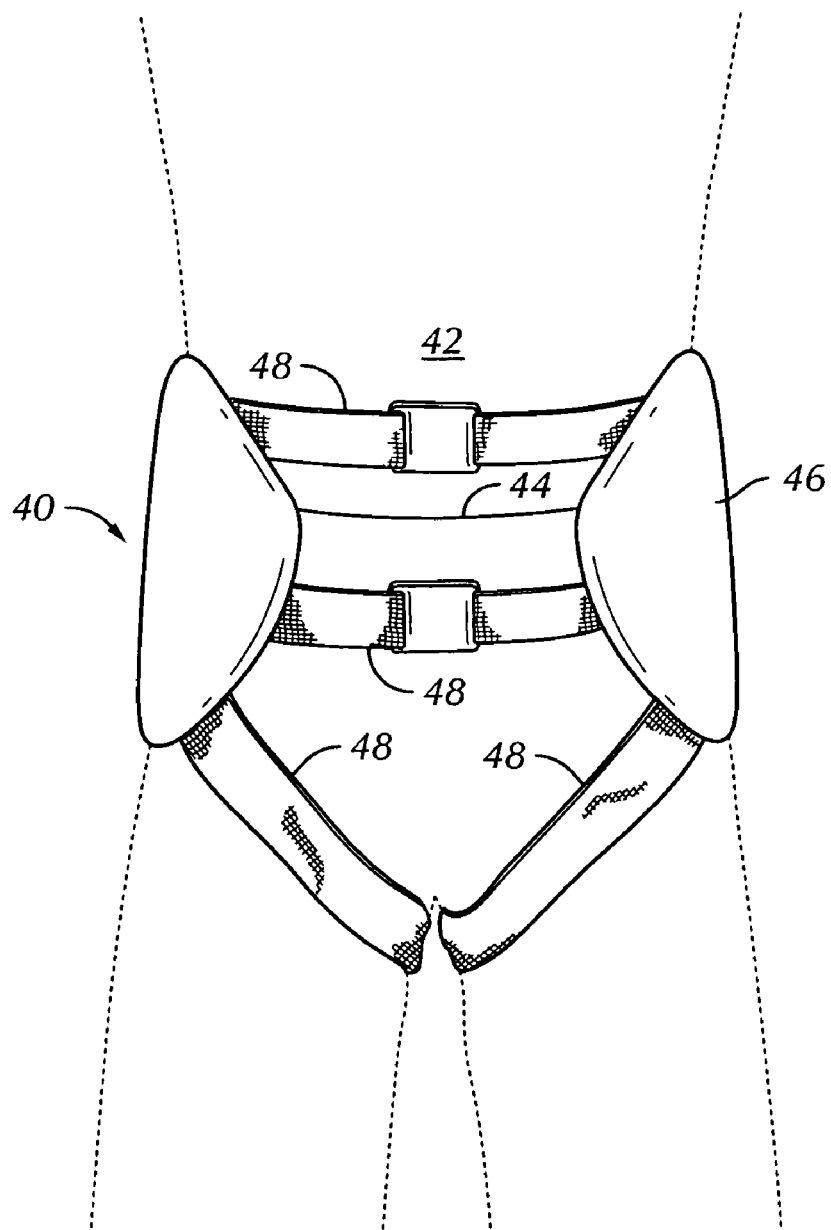
FIG. 4 is a front view of the mid-section of a human to which one embodiment of a human-attachment element of one of the present endoscope-securing apparatuses has been attached.
Figure 5:
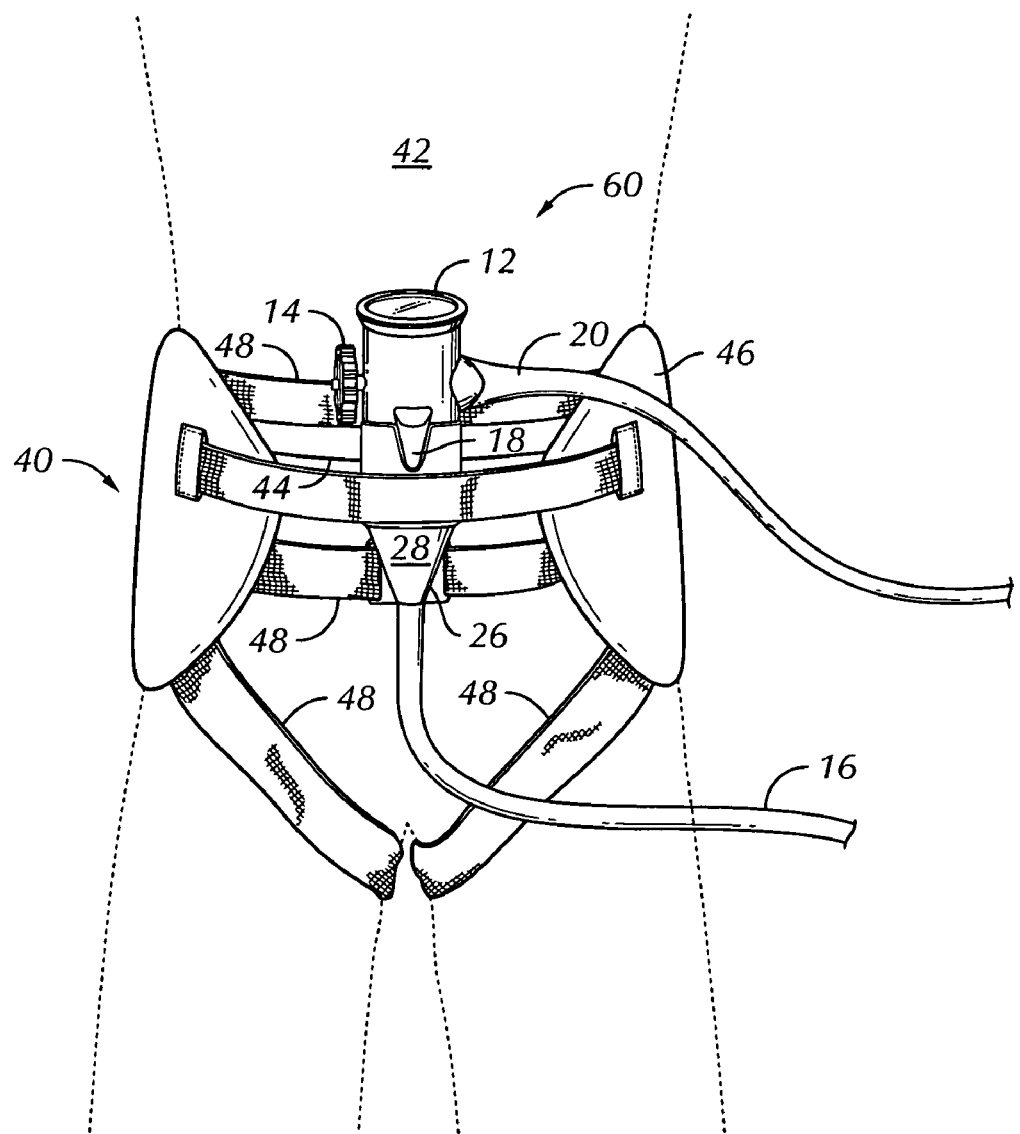
FIG. 5 is a front view of one embodiment of the present endoscope-securing apparatuses.

FIG. 4 depicts human-attachment element 40 attached to human 42. As shown, human-attachment element 40 is a harness that is secured to the mid-section of human 42 near the waist of human 42, which is represented by waistline 44. Human-attachment element 40 includes mid-section 46 and a human-attachment system for attaching human-attachment element 40 to human 42. In FIG. 4, this human-attachment system is depicted as a strap system illustrated as straps 48. The strap system may be configured to include as many straps as are necessary for ensuring secure attachment of human-attachment element 40 to human 42. This may involve only one strap, as many as 5 straps, or even more.

Figure 6:
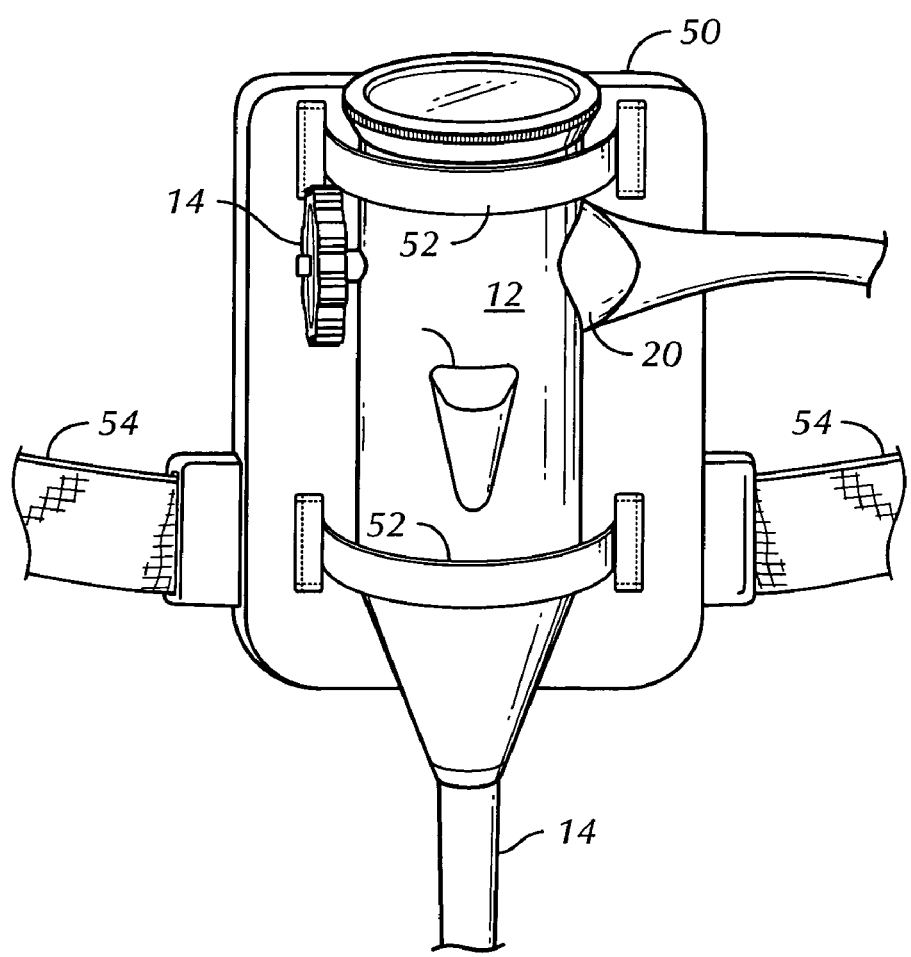
FIG. 6 is a front view of another embodiment of an endoscope-securing element of one of the present endoscope-securing apparatuses, which endoscope-securing element is depicted as being in contact with an endoscope.

Turning next to FIG. 6, another embodiment of endoscope-attachment apparatus 26 is shown. This embodiment includes base 50 to which endoscope 10 is secured using an endoscope-securing mechanism. As shown in FIG. 6, this endoscope-securing mechanism takes the form of endoscope-securing straps 52. Base 50 may be made of any suitable material or polymer, such as plastic or rubber, or a lighter material such as STYROFOAM. Base 50 may be configured or molded such that endoscope 10 does not easily slip once in position against it.

While the endoscope-securing mechanism provided on base 50 is illustrated as a pair of straps in FIG. 6, those of skill in the art having the benefit of this disclosure will understood that an endoscope-securing mechanism may take any suitable form, such as buckles, VELCRO, adhesive, knot(s), tape, interlocking parts (e.g., snaps), or the like. Alternatively, base 50 may be formed with an opening into which endoscope 10 may be placed, thereby taking advantage, for example, of the force of gravity and eliminating the need for an endoscope-securing mechanism. Alternatively or additionally, such an opening in base 50 may take the form of a pocket equipped with any of the attachment means described above, which may, in turn, be used to keep endoscope 10 securely positioned in the pocket.

Figure 7:
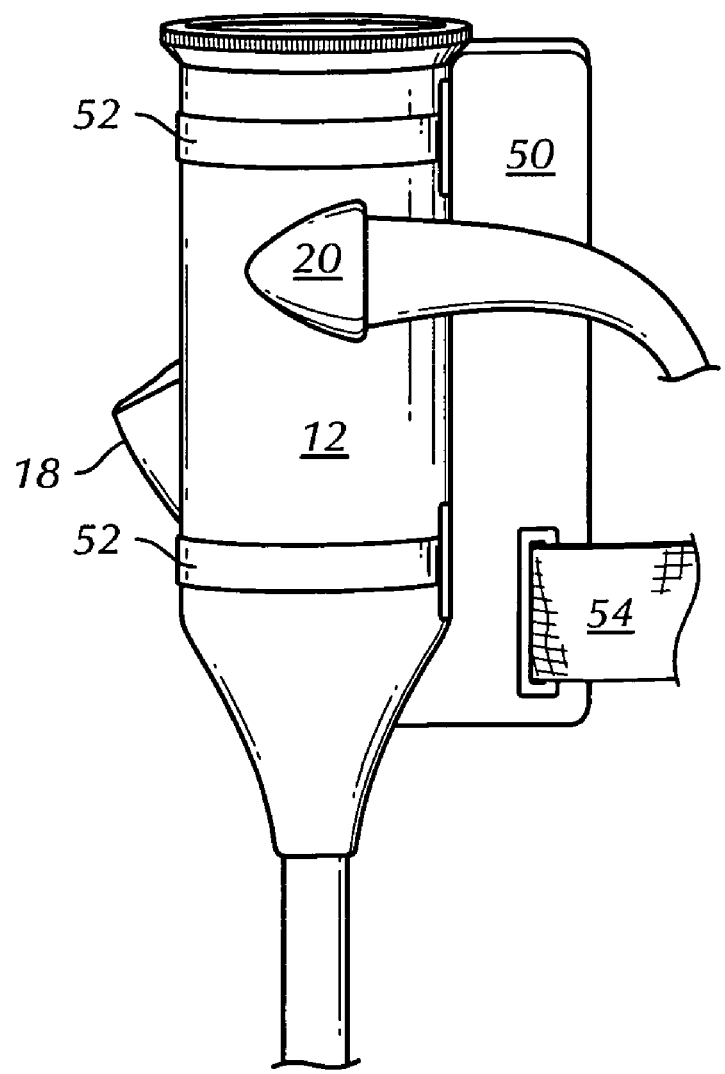
FIG. 7 is a side view of the arrangement depicted in FIG. 6.

FIG. 7 is a side view of the embodiment of endoscope-attachment apparatus 26 shown in FIG. 6.

Figure 8:
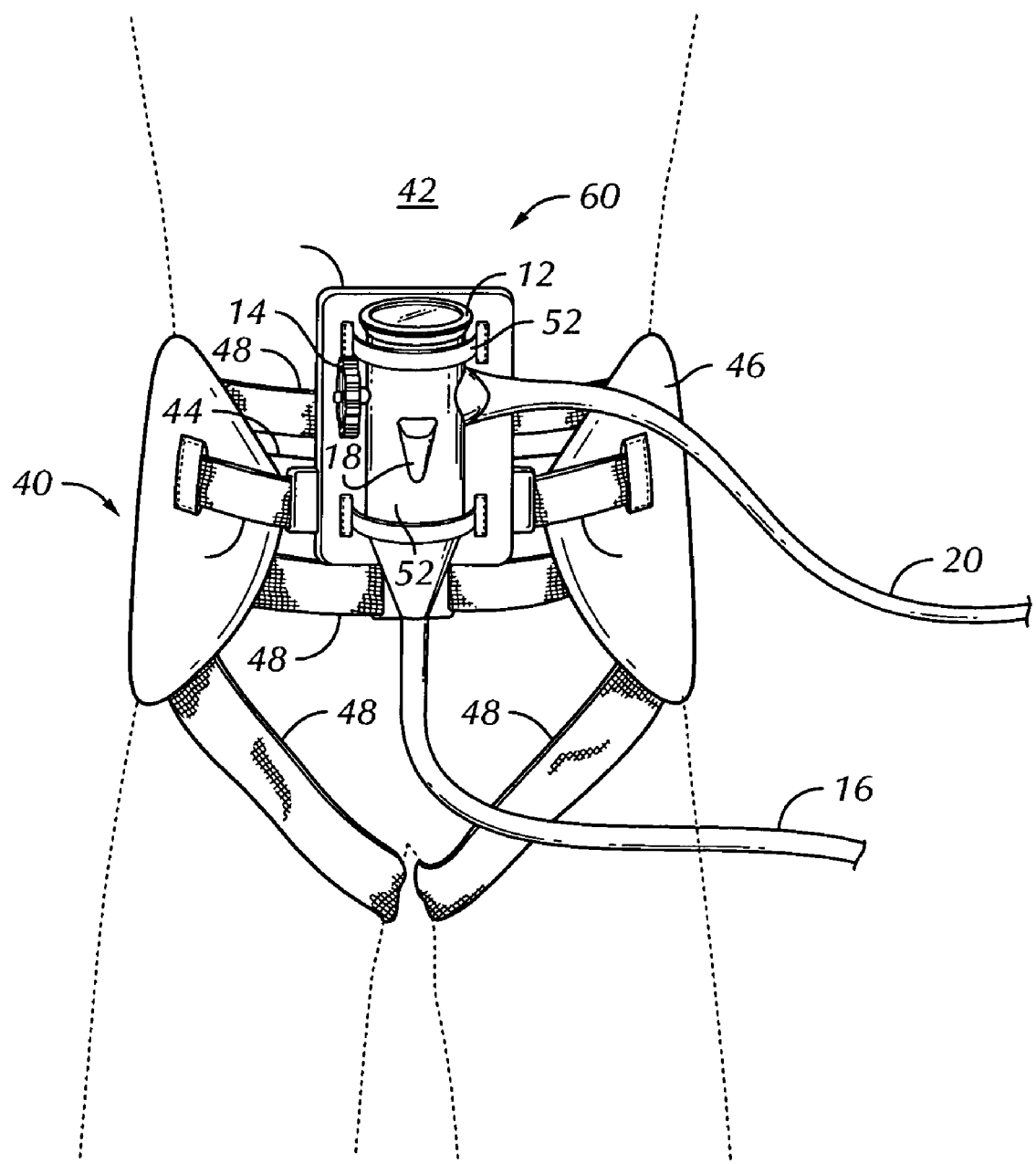
FIG. 8 is a front view of another embodiment of the present endoscope-securing apparatuses.

As shown in FIG. 6, base 50 may be provided with harness-attachment elements 54 that may be used to attachment base 50, and thus endoscope 10, to human-attachment element 40 as shown in FIG. 8. Together, human-attachment element 40 and endoscope-attachment element 26 form another embodiment of endoscope-securing apparatus 60, as shown in FIG. 8.

Example of endoscopes that may be secured to a human using one of the present endoscope-securing apparatuses and manipulated using the present methods include any of Olympus's endoscopes, which may be found at Olympus's website at olympus.com. One suitable endoscope is the Olympus GIF 2T 200. Further, an example of a human-attachment element 40 that takes the form of a harness is a harness that may be used is a windsurfing harness. One such windsurfing harness is the DA KINE SLALOM SEAT.

In configuring the human-attachment and endoscope-attachment elements of the present endoscope-securing apparatuses, care should be taken to provide a configuration that results in positioning an endoscope (or other medical device) relative to the surgeon at an ergonomic location for the surgeon's hands. That is, the endoscope should be located in a position that will allow the surgeon to reach for and control the endoscope with his hands on occasions when it is necessary for the surgeon to do so without having to overextend or bend his arms. Similarly, any accessory-acceptance projection should be located in a position that allows the surgeon to easily control any accessories placed in such a projection with his hands.

Turning to the present methods, one such method facilitates the manipulation of an endoscope. This involves providing an endoscope, and securing it to a human such that a surgeon may move it, or manipulate it, using one or more hands-free movements. Such movements can be achieved as described above. Also, the securing may be achieved as illustrated, for example, in FIGS. 5 and 8. That is, the endoscope may be secured to the human near his waist using, for example, a human-attachment element (e.g., a harness) such as the one depicted in FIG. 4.

Another of the present methods involves manipulating an endoscope after securing it to a human. The manipulation may include causing the endoscope to move using one or more hands-free movements. The human may make a hands-free movement in one direction that causes the endoscope to move in the same direction. As used, herein, a first direction that is the same as a second direction need not be characterized by the same vectors that characterize the second direction. Instead, the first and second directions need only share at least one of the same vectors to be the same within the meaning of this disclosure. With this embodiment, the endoscope may be secured to the human near his waist using, for example, a human-attachment element (e.g., a harness) such as the one depicted in FIG. 4. An accessory may be inserted into an accessory-acceptance projection of the endoscope and manipulated with one or both of the human's hands.

In another embodiment of the present methods, a hands-free movement in one direction having a certain magnitude will not necessarily cause the endoscope to move in the same direction with the same magnitude. For example, if a rotational hands-free movement is made (e.g., a twist of the torso), the same degree of rotation may not be duplicated in the endoscope. For example, the degree of rotation of the endoscope may be less. Alternatively, the degree of rotation of the endoscope may be more.

What is claimed is:

1. A method of manipulating an endoscope, comprising: securing the endoscope to a human's mid-section, the endoscope having:
   an insertion tube having at least one passageway, and
   an accessory-acceptance projection in communication with the at least one passageway, the accessory-acceptance projection being configured to accept one or more accessories; and
   manipulating the endoscope through at least one or more hands-free movements of the human.

2. The method of claim 1, where the endoscope is secured to the human near the waist of the human.

3. The method of claim 1, where the securing comprises: attaching a harness to the human; and
   securing the endoscope to the harness near the waist of the human.

4. The method of claim 1, where the manipulating comprises moving the endoscope in a first direction through a hands-free movement of the human in the same direction.

5. The method of claim 1, further comprising:
   inserting an accessory into the accessory-acceptance projection; and
   manipulating the accessory with one or both of the hands of the human.

* * * * *